the# United States Patent [19]

Caugant et al.

[11] Patent Number: 4,541,293
[45] Date of Patent: Sep. 17, 1985

[54] LOAD-BEARING TELESCOPIC SLIDE ASSEMBLY AND X-RAY INSTALLATION EQUIPPED THEREWITH

[75] Inventors: Jean Caugant; Jacques Dale, both of Paris, France

[73] Assignee: Thomson CSF, Paris, France

[21] Appl. No.: 391,436

[22] Filed: Jun. 23, 1982

[30] Foreign Application Priority Data

Jun. 23, 1981 [FR] France ................................. 81 12297
Mar. 12, 1982 [FR] France ................................. 82 04213

[51] Int. Cl.$^4$ .............................................. F16H 19/04
[52] U.S. Cl. ...................................... 74/89.18; 74/110; 74/422
[58] Field of Search ................... 74/110, 89.17, 89.18, 74/422

[56] References Cited

U.S. PATENT DOCUMENTS

| 250,233 | 11/1881 | Griest | ..................................... | 74/422 |
|---|---|---|---|---|
| 968,312 | 8/1910 | Bacon | ..................................... | 74/422 |
| 1,637,352 | 8/1927 | Reaney | ..................................... | 74/110 |
| 1,705,110 | 3/1929 | Goldsmith et al. | ..................... | 74/422 |
| 2,182,985 | 12/1939 | Henry . | | |
| 2,588,124 | 3/1952 | Kizaur . | | |
| 2,880,897 | 4/1959 | Wilms et al. | ........................... | 74/110 |
| 3,244,883 | 4/1966 | Labus . | | |
| 3,396,601 | 8/1968 | Wright | ................................. | 74/110 |
| 3,665,771 | 5/1972 | Blatt | ..................................... | 74/422 |
| 3,838,286 | 9/1974 | Prendergast . | | |

FOREIGN PATENT DOCUMENTS

| 69463 | 12/1975 | Australia . |
|---|---|---|
| 0015612 | 2/1980 | European Pat. Off. . |
| 1466883 | 6/1969 | Fed. Rep. of Germany . |
| 2120344 | 12/1971 | Fed. Rep. of Germany . |
| 1071714 | 9/1954 | France . |
| 987721 | 9/1964 | France . |
| 1490958 | 6/1967 | France . |
| 1572841 | 6/1969 | France . |
| 2264363 | 10/1975 | France . |
| 916178 | 1/1963 | United Kingdom . |
| 2056830 | 3/1981 | United Kingdom . |
| 2086700 | 5/1982 | United Kingdom . |

Primary Examiner—Lawrence Staab
Attorney, Agent, or Firm—Cushman, Darby & Cushman

[57] ABSTRACT

A compact load-bearing slide assembly, especially for use in an X-ray installation. This assembly substantially comprises two supports 1, 3, the second of said supports 3 bearing the load. The two supports are coupled laterally by a median carriage 2. The assembly is able to be extended telescopically under the action of first actuating means 9 moving the carriage with respect to the first support, and second actuating means 13 moving the second support with respect to the carriage. The novel slide assembly is especially advantageous when used for cardiovascular X-ray examination.

3 Claims, 2 Drawing Figures

LOAD-BEARING TELESCOPIC SLIDE ASSEMBLY AND X-RAY INSTALLATION EQUIPPED THEREWITH

SUMMARY STATEMENT OF THE FIELD OF THE INVENTION

The present invention is related to a load-bearing slide assembly particularly adapted to be used in X-ray installations. The invention is more particularly related to such slide assembly which has a telescopic construction and the space requirement of which is minimum in the rest position, while said slide assembly is able to effect movements of great magnitude in either direction from said rest position.

SUMMARY DESCRIPTION OF THE PRIOR ART

An X-ray installation comprises at least one examination table onto which a patient is placed, an X-ray source and an image receiver associated, in many cases, with a luminance amplifier. The source and the receiver are located on opposite sides of the table, respectively. In the course of an examination it is often required to vary the incidence of the X-ray with respect to the patient. Consequently the source and receiver must be movable with reference to the examination table. These two devices however are heavy and bulky. Therefor their supports are generally constituted by large-size elements so as to be prevented from flexing under the load.

SUMMARY STATEMENT OF THE AIM OF THE INVENTION

The present invention is aimed at providing an assembly which is more compact and less expensive than the prior assemblies of the type considered.

Another object of the invention is to provide such assembly which is able to carry out tomographic movements at high speed. Indeed, when carrying out tomographic examination, any vibration of the moving source or receiver must be avoided with a view to preventing the image formed on the receiver from being disturbed. It is thus an object of the invention to provide an assembly of the kind defined herein-above which also allows this particular complementary problem to be solved in a highly satisfactory manner.

SUMMARY DEFINITION OF ONE ASPECT OF THE INVENTION

With these and other aims and objects in view the invention is directed to a load-bearing telescopic slide assembly comprising a first support, a second support bearing said load, said second support being similar to the first support and movable in either direction with respect to the same, said supports being coupled to each other by a median carriage, said carriage and said supports being provided with respective sliding means, first actuating means for displacing said carriage with respect to said first support, and second actuating means for displacing said second support with respect to said carriage.

The invention is also directed to an X-ray installation using slide assemblies of the kind defined herein-above.

BACKGROUND OF THE INVENTION

It is known that certain cases X-ray examination of the heart requires two explorations with different respective incidences so as to provide more precise images of the heart cavities and allow their volume to be determined. These examinations are carried out by injecting so-called contrast products into the blood system, or sanguineous system. Such products are not well supported by the organism and may even be the cause of an interruption of the cardiac function during the examination, whereby it becomes necessary to effect revival of reanimation operations. Thus it is desirable, on the one hand, to reduce to a minimum the amount of contrast product used and, on the other hand, to provide an X-ray installation which does not hamper the work of the reanimation team and which preferably can be removed very quickly from the patient.

With a view to reducing the amount of injected contrast product it has already been proposed to use an installation comprising two source-and-receiver systems arranged about an analysing center located in the vicinity of the table on which the patient is placed, these two systems being adapted to be actuated simultaneously, whereby only one single injection of constrast product is required. Such installation essentially comprises two large bow elements substantially defining half-circles, each one of said bow elements bearing at its two ends an X-ray source and a receiver (associated to a luminance amplifier), respectively. A guiding rail is provided along each bow element, and a support movable with respect to the table meshes with this rail. Thus when it is desired to vary the incidence of the X-rays during examination the entire assembly constituted by the bow element, the source and the receiver is moved along a circular path. An installation of this type operates satisfactorily and enables, in particular, to reduce the amount of contrast product used in cardiovascular examination or exploration. However on account of their volume the bow elements may render difficult the access to the patient; this applies especially to one of said elements which is arranged so as to have a fictive rotational axis parallel to the table. Furthermore, in such installation the cantilevered masses are considerable and require heavy structures, and consequently only the biggest hospitals can be equipped with this kind of installation.

Due to the use of a plurality of slide assemblies of the above described type, an installation according to the invention is less complex and less expensive than an installation using two bow elements. Furthermore the novel installation is less prone to impede the access to the patient, and it is also possible to remove said installation very quickly in case of an emergency.

SUMMARY DEFINITION OF ANOTHER ASPECT OF THE INVENTION

With a view to obtain the above-mentioned advantages the invention provides an X-ray installation comprising two source-and-receiver systems arranged about an analysing center, one of said systems being a main system substantially comprising a support having two arms rotatively movable about a horizontal axis, a radiation source supported by one of said arms and a receiver supported by the other arm, the other system being a supplementary system adapted to be used for X-ray examinations wherein simultaneous vision of a given area with two selected different incidences is required, said supplementary system comprising a lower movable sub-assembly and an upper movable sub-assembly independent of said lower sub-assembly, said sub-assemblies supporting a source and a receiver, respectively, which are adapted to be positioned respectively on opposite sides of said analysing center, said source and said receiver being mounted on their respective sub-assemblies by means of telescopic slide-assemblies having the shape of circular ring sectors, which are so oriented that they are enabled to move in vertical planes.

Thus one of the above-mentioned bow elements (to wit: the bow element having a fictive rotational axis parallel to the axis of the table) is now replaced by two extremely mobile sub-assemblies one of which moves, for example, along a guiding structure fixed to the ceiling of the examination room, while the other sub-assembly, in the form of a rolling carriage is placed in the desired position underneath the examination table.

The invention will be described herein-below in more detail, especially with reference to the appended Figures which are given by way of illustration, but not of limitation.

BRIEF DESCRIPTION OF THE DRAWING

In the appended drawing

DETAILED DESCRIPTION OF PREFERRED EMBODIMENTS OF THE INVENTION

Figure 1:
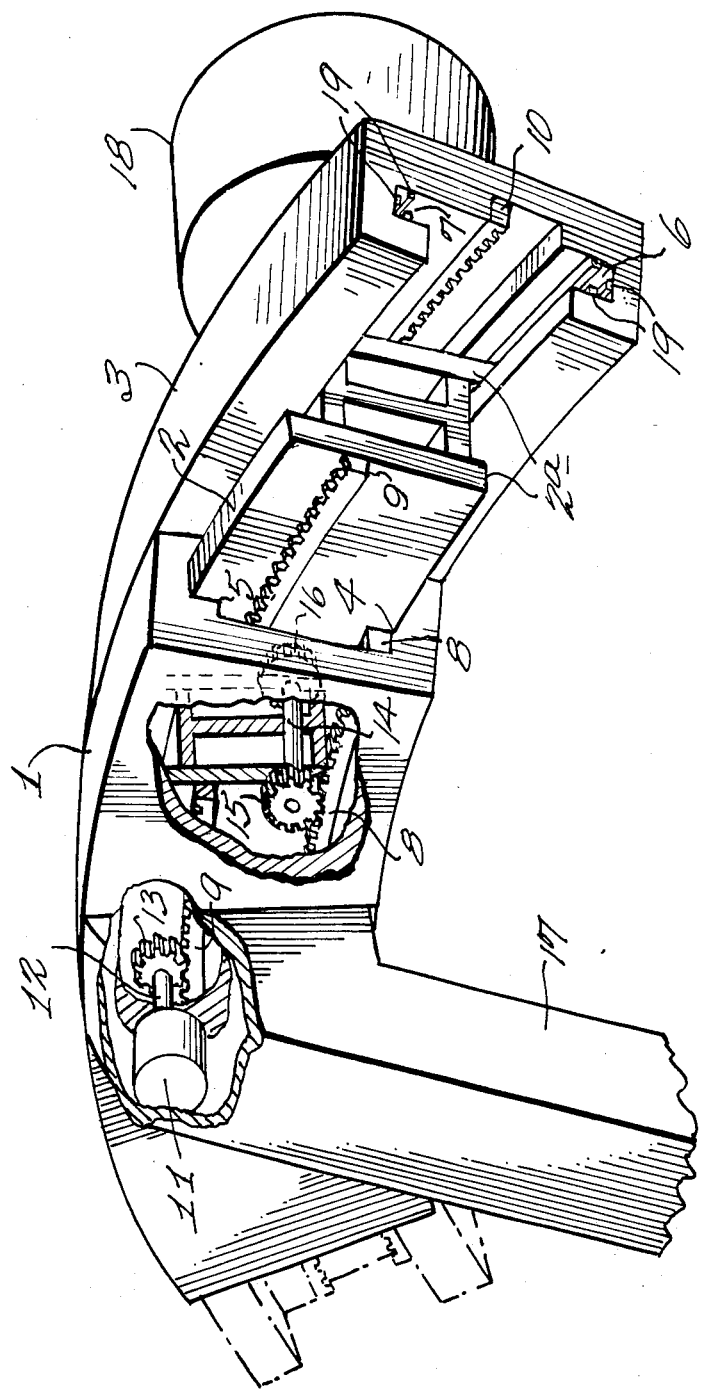
FIG. 1 is a perspective view of a load-bearing slide assembly according to the invention.

As shown in FIG. 1 the slide assembly according to the invention substantially comprises three elements slidingly movable with respect to each other, to wit: a first support 1, a second support 3 bearing a load 18, which second support is similar to the first support 1 and movable and extendable in either direction with respect to the latter, as well as a median carriage 2 adapted to couple laterally said supports to each other. The supports and the carriage have the general shape of a sector of a circular ring. The supports have a cross-section defining the general shape of a "C", whereas the carriage has a cross-section defining the general shape of an "H". As shown, these three elements are coupled laterally to each other and movable with respect to each other along circular paths parallel to the curvature of said elements. The opposite recessed surfaces of supports 1 and 3 receive median carriage 2 which laterally couples supports 1 and 3 to each other by means of ribs 2a defined by the H-shaped profile of the carriage, and by means of grooves forming slide tracks 4, 5 and 6, 7 defined respectively by the C-shaped supports 1 and 3. Each slide is provided with three fillets 19 adapted to facilitate the sliding motion of the carriage with respect to the first support, on the one hand, and of the second support with respect to the carriage, on the other hand. These fillets are made of an organic polymer material of the type currently named PTFE or PYDANE. The load 18 supported by second support 3 may be constituted, in the field of X-ray installations, by an X-ray source or receiver associated to a luminance amplifier.

The system is completed by means for actuating the carriage with respect to the first support, on the one hand, and by means for actuating the second support with respect to said carriage, on the other hand. These actuating means are coupled mechanically to a single driving motor 11 which is mounted integrally, in the embodiment shown, with the first support 1 and encased in an inner space defined by a column 17 maintaining the assembly at a certain distance from the patient. The means for actuating or moving the carriage 2 with respect to the first support 1 comprise a first rack-bar 9 which is curved and mounted to the carriage and which meshes with a pinion 13 mounted on the shaft 12 of motor 11. Furthermore the means for actuating or driving the second support 3 with respect to carriage 2 comprise a shaft 14 mounted transversely on carriage 2, so as to be free to rotate, said shaft 14 having at each one of its two ends a pinion 15, 16. Pinion 15 meshes with a second rack-bar 8 having a curved shape which is associated to the first support 1, while pinion 16 meshes with a third rack-bar 10 having a curved shape and being mounted to the second support 3, said third rack-bar extending parallely to said second rack-bar 8. The respective teeth of rack-bars 8 and 10 are mutually opposed and located in two parallel planes.

The device described herein-above operates as follows:

When motor 11 rotates in a clock-wise direction pinion 13 drives carriage 2 so as to move it toward the right side, with reference to FIG. 1; at the same time the assembly constituted by shaft 4 and the two pinions 15 and 16 is rotated due to the meshing of pinion 15 with rack-bar 8. Thus pinion 16 meshing with rack-bar 10—which latter is mounted symmetrically with respect to shaft 14 relative to rack-bar 8 - displaces second support 3 with respect to carriage 2 in the same direction. Pinions 15 and 16 may have identical diameters, whereby a given magnitude of displacement of carriage 2 with respect to the first support corresponds to a displacement of twice this magnitude of the second support.

In another embodiment of the invention supports 1 and 3 may be rectilinear.

One of the main advantages of the slide assembly described herein-above resides in that it allows a heavy load to be displaced rapidly without requiring a displacement of column 17 itself. Indeed in the field of X-ray examination it is known that angular displacements are obtained by a rotational movement of the column about a fixed axis. Due to the elevated weight of the load the column must be of large dimensions so as to be able to accomodate the considerable acceleration forces involved. Since the slide assembly according to the invention is the only movable part, it is thus rendered possible to associate it to a comparatively light column. Such column 17 may be mounted onto a movable carriage, for example on a horizontal rail.

Figure 2:
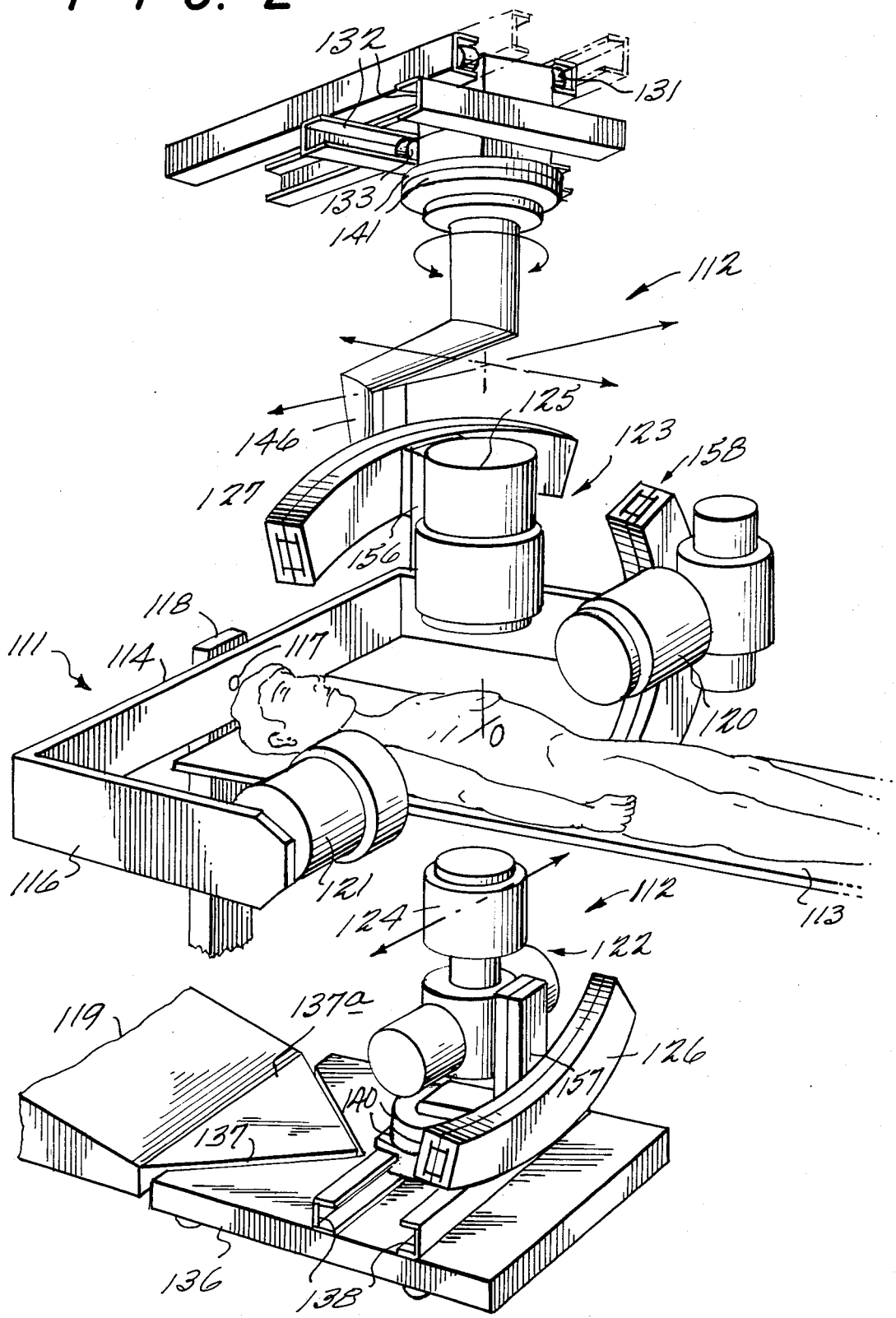
FIG. 2 is a diagrammatical overall view in perspective and represents an X-ray installation comprising two slide
assemblies similar to that shown in FIG. 1.

The X-ray installation shown in FIG. 2 represents an advantageous application of the invention, which clearly illustrates the outstanding properties of the above-described slide assembly. This installation substantially comprises two source-plus-receiver units or systems 111 and 112 which are disposed about an analysing center 0 defined at a distance of several centimetres above a table 113 on which a patient is adapted to be placed. System 111, or "main system", comprises a support 114 having two parallel arms 115, 116 rotatable about an horizontal axis 117 of a fixed support 118 reposing on the floor through the intermediary of a base 119. Arm 115 supports at its end a X-ray source 120 and arm 116 supports at its end a receiver 121 associated to a luminance amplifier. Source 120 and receiver 121 associated to the luminance amplifier are located opposite to each other on either side of analyzing center 0. System 112, or "supplementary system", is mainly provided for utilisation during examinations where it is required to obtain simultaneous vision of one given region or area under two different selected incidence angles, e.g. especially during cardiovascular examinations. This system mainly comprises two movable, independent sub-assemblies 122, 123. Lower sub-assembly 122 supports an X-ray source 124 similar to source 120 while upper sub-assembly 123 supports a receiver 125 similar to receiver 121. It is possible however to reverse this arrangement, i.e. receiver 125 may be supported by sub-assembly 123. Such arrangement is advantageous when it is desired to submit babies or infants to X-ray examination, since in this case receiver 125 having a large volume as compared to the size of the infant is then placed under the table and does not in any way hamper the examination carried out by the physician, or practitioner. As clearly shown in FIG. 2, source 124 and receiver 125 are placed opposite to each other on either side of analysing center 0 when supplementary system 112 is placed in its utilising position. According to an important feature of the invention source 124 and receiver 125 are mounted to onto their respective sub-assemblies with the interposition of slide assemblies 126 and 127 having the shape of circular ring sectors. When the sub-assembly is in its working position the center of the ring sectors coincides with the analysing center 0 mentioned hereinabove. These slide assemblies correspond to the one described hereinbefore. Thus in the position corresponding to the minimum space requirement (i.e. the rest position, or neutral position), such as illustrated in FIG. 2, any given slide assembly extends only over a small portion of the ring sector, corresponding to a central angle of 30°, while the source (or the receiver) is able to be displaced by ±30° with respect to said central position shown in the figure, when the telescopic slide assembly reaches the end of its stroke length at one side or the other of said central position.

Upper sub-assembly 123 is movable along guiding rails 130 fixed to the ceiling of the room wherein the installation is mounted, the motions of said sub-assembly being effected in a direction parallel to table 113. Said rails support rollers 131 associated to a median (or intermediary) carriage substantially defined by two small straight parallel rails 132 extending perpendicularly to rails 130, and along which sub-assembly is adapted to move at a small perpendicular distance from the table by means of rollers 133. This small clearance enables to align accurately receiver 125 with respect to the organ to be observed of the patient, e.g. the heart.

Lower sub-assembly 122 is mounted on a carriage 136 rolling on the floor and is provided with positioning and locking means in the form of a V-shaped recess 137 cooperating with complementary means fixed to the floor and constituted, for example, by a pointed portion 137a of the base 119. Sub-assembly 122 is mounted on its carriage by means of two other small, parallel straight rails 138 along which it is adapted to be displaced. Rails 138 are parallel to rails 132, when the carriage is maintained in a working position such as shown in the figure. Sub-assemblies 122 and 123 are provided with locking means (not shown) adapted to block the sub-assemblies in any desired position or location along rails 132 and 138, respectively; convenient positions, maintaining the coaxial relationship of the optical axes of the source and the receiver, will be determined either by simple mechanical means or by conveniently coupling two motors (not shown) which displace the sub-assemblies along the corresponding rails 132 and 138. On the other hand, rails 130 are provided mainly for bringing sub-assembly 122 to a position above the patient; stop members (not shown) are consequently provided for positioning said sub-assembly at a selected location above table 113. Rails 132 could also be omitted, and rails 130 could then be oriented perpendicularly with reference to the position shown, while sub-assembly 123 moves directly on these rails 130, means being provided, in this case, for locking said sub-assembly at a selected location near the end of the stroke with a view to ensuring correct alignment of the source and the receiver.

Furthermore every sub-assembly 122, 123 is provided with a joint or articulation 140, 141 having a vertical axis, such joints comprising each for example two coupled circular flanges angularly movable with respect to each other. Joint 140 of sub-assembly 122 is located between rails 138 and slide assembly 126, while joint 141 of sub-assembly 123 is interposed between rails 132 of the above-mentioned median carriage and a cranked leg 146 fixed to slide assembly 127. In both cases the geometrical disposition of the components of sub-assemblies 122 and 123 is such that the rotational axis of joint 140 or 141 coincides with the main axis of symmetry of source 124 or receiver 125 when each one of the corresponding slide assemblies 126, 127 is located in its central position defining minimum space requirement, as shown in FIG. 2, i.e. in a position wherein the two outer elements of the slide assembly considered are entirely facing each other. Thus the combination of the rotational movements at joints 140 and 141 and the pivotal movement along slide assemblies 126 and 127 enables source 124 and receiver 125 to explore each a conical area having a given apex angle (for instance 60°), the apex of which coincides with analysing center 0. A selected incidence of the source within the limits of its conical displacement area will of course determine automatically a specific orientation of the receiver in such a manner that the latter is located substantially opposite to the source and aligned substantially with a line passing through the analysing center. In praxis this result is achieved by maintaining slide assemblies 126, 127 in parallel planes and by conferring on said assemblies identical curved extensions according to a common direction of rotation. It is possible, too, of course, to provide to this end any convenient known coupling means of a mechanical and/or electronic nature with a view to maintain the source and the receiver in an isocentric position with reference to analysing center 0.

Furthermore, the conventional technique of radiological magnifying or enlarging requires the possibility of displacing the receiver with respect to the patient along its axis of alignment with the source. To this end, receiver 125 is mounted, as shown, on its slide assembly 127 by means of a system of straight slide tracks 156 parallel to a radial direction passing through the center of the second support 147 (which bears the receiver) of slide assembly 127. A similar system of straight slide tracks 157 is provided between source 124 and slide assembly 126. This arrangement is justified by the above-mentioned fact that it is sometimes required to reverse the source and receiver with respect to sub-assemblies 122 and 123 when carrying out pediatric examinations.

It should also be noted that arm 115 of the main system 111 which bears source 120 is also equipped with a slide assembly 158 similar to slide assemblies 126 and 127, said assembly 158 being interposed between said arm and said source. When cardiovascular X-ray examinations are carried out this slide assembly will be maintained in its central position (corresponding to extension zero), as shown.

However for certain examinations, especially examinations of the skull it may be desirable to confer on the X-ray beam a supplementary incidence with respect to the receiver. Slide assembly 158 enables to do this without substantially increasing the space requirement and/or the cost of the installation.

The operating mode of this installation is obvious in the light of the above description. When it is desired to carry out an examination with two simultaneous different incidences, it is only necessary to bring carriage 136 (which supports the X-ray source) under the table 113 and to position it in engagement with the end of base 119, while displacing sub-assembly 123 along rails 130 until receiver 125 is placed at the correct location above the patient. The alignment of the source and the receiver is then correctly adjusted by adjusting the respective positions of the sub-assemblies on rails 138 and 132, in such a manner that the common axis of the source and the receiver passes through the organ to be examined. A selected incidence angle is entirely determined by turning articulations (or joints) 140 and 141 (the slide assemblies being maintained parallel to each other) and by identical extensions of the slide assemblies.

If reanimation is required sub-assembly 122 does not disturb the personnel, while sub-assembly 123 may easily be removed to a convenient distance by displacement along rails 130.

The invention is not limited to the embodiments shown and described herein-above; many variants and modifications may be envisaged by those skilled in the art without departing from the spirit and scope of the invention as defined in the appended claims.

What is claimed is:

1. A load-bearing slide assembly for an X-ray installation comprising:
   a fixed first support having the general shape of a circular ring sector with a substantially C-shaped cross-section, said cross-section opening laterally and having grooves forming slide tracks;
   a mobile second support for carrying said load in either direction with respect to said first support having the general shape of a circular ring sector with a substantially C-shaped cross-section and having grooves forming slide tracks, said cross-section having a lateral opening facing the opening of said fixed support;
   a median carriage having the shape of a circular ring sector and an H-shaped cross-section cooperating with said supports with respective parallel ribs engaging the slide tracks of said first and second supports;
   means for displacing said carriage with respect to said first support including a first arc-shaped rack-bar, a shaft having a pinion at one end engaging said first rack-bar and a motor for rotating said shaft; and
   means for displacing said second support with respect to said carriage including a second arc-shaped rack-bar mounted to said first support, a third arc-shaped rack-bar mounted to said second support, and a freely rotatable shaft mounted for movement with said carriage and having a pinion at each end respectively engaging said second and third rack-bars.

2. An assembly as in claim 1 wherein said motor is fixed to said first support and said first rack-bar is integral with said carriage.

3. An assembly as in claim 1 wherein said slide tracks are provided with fillets of polymer organic material.

* * * * *